United States Patent
Stockard

(10) Patent No.: US 7,153,470 B2
(45) Date of Patent: Dec. 26, 2006

(54) METHOD OF MODELING SANITATION LEVELS IN FOOD PROCESSING EQUIPMENT

(75) Inventor: Richard Daniel Stockard, Kirkland, WA (US)

(73) Assignee: FMC Technologies, Inc., Chicago, IL (US)

( * ) Notice: Subject to any disclaimer, the term of this patent is extended or adjusted under 35 U.S.C. 154(b) by 838 days.

(21) Appl. No.: 10/094,690

(22) Filed: Mar. 8, 2002

(65) Prior Publication Data

US 2003/0171943 A1    Sep. 11, 2003

(51) Int. Cl.
*A61L 2/24* (2006.01)

(52) U.S. Cl. .............................. 422/3; 422/26; 422/28; 422/105; 422/292; 700/29; 700/30; 702/136; 705/1

(58) Field of Classification Search .................... 422/3, 422/26, 28; 705/1; 700/29, 30; 702/136
See application file for complete search history.

(56) References Cited

U.S. PATENT DOCUMENTS

| | | | |
|---|---|---|---|
| 4,340,610 A * | 7/1982 | Nioras | 426/88 |
| 4,990,347 A * | 2/1991 | Rasmussen et al. | 426/232 |
| 5,254,474 A | 10/1993 | Kim | |
| 5,293,753 A | 3/1994 | Rothstein et al. | |
| 5,451,369 A | 9/1995 | Daeschel et al. | |
| 5,474,910 A * | 12/1995 | Alfano | 435/34 |
| 5,552,114 A | 9/1996 | Till | |
| 5,900,801 A | 5/1999 | Heagle et al. | |
| 5,939,974 A | 8/1999 | Heagle et al. | |
| 5,941,257 A | 8/1999 | Gruszczynski, II | |
| 6,039,984 A * | 3/2000 | Bowling et al. | 426/61 |
| 6,080,435 A * | 6/2000 | Rubow et al. | 426/235 |
| 6,264,889 B1 | 7/2001 | Tottenham et al. | |
| 2001/0046537 A1 | 11/2001 | Weng | |

* cited by examiner

Primary Examiner—Krisanne Jastrzab
(74) Attorney, Agent, or Firm—Christensen O'Connor Johnson Kindness PLLC

(57) ABSTRACT

A method of creating a sanitation level model with respect to a predefined microorganism in food processing equipment is provided. The method includes generally three steps. First, a temperature history during a use cycle of the food processing equipment is created. The temperature history includes a collection of a plurality of temperatures that the food processing equipment undergoes during the use cycle. The use cycle includes a normal use stage, a sanitizing stage, and perhaps an idle stage. Second, a growth model of the microorganism is continuously applied to each applicable temperature in the temperature history. Third, a death model of the microorganism is continuously applied to each applicable temperature in the temperature history. The created sanitation level model is used to ascertain the microorganism growth/death rate in the food processing equipment during the use cycle.

19 Claims, 6 Drawing Sheets

METHOD OF MODELING SANITATION LEVELS IN FOOD PROCESSING EQUIPMENT

FIELD OF THE INVENTION

The present invention is directed to a method of quantifying sanitation levels in food processing equipment, and more particularly, to such method of modeling sanitation levels regarding certain microorganisms of interest (e.g., pathogens) using known growth and death models of the microorganisms.

BACKGROUND OF THE INVENTION

Control of microorganisms in food plants is required to ensure the safety of the food being processed. The Hazard Analysis and Critical Control Points (HACCP) system is a food processing control system that seeks to prevent food safety problems. Using a HACCP plan, a company analyzes its processes to identify areas of risk and concentrates its monitoring and prevention resources at those critical points. In particular, predetermined actions must be available to correct the processes if a control point goes beyond its predetermined limits. HACCP plans became mandatory for federally inspected U.S. meat and poultry plants beginning in 1998. More recently, the Food Safety and Inspection Service (FSIS) has issued new "science based" HACCP regulations, together with accompanying Sanitation Standard Operating Procedures (SSOPs) and Good Manufacturing Practices (GMPs), which are designed to encourage companies to monitor and prevent the microbiological contamination of foods during processing. "Science based" sanitation quantification means that a level of microbiological contamination, for example the amount of pathogenic bacteria present during food processing, is quantified with much greater accuracy as compared to "non-science based" sanitation quantification, such as visual inspection of food equipment. Visual inspection of equipment surfaces is not sufficient to determine the cleanliness of equipment if the hazard being measured is bacterial. "Science based" quantification of sanitation procedures, however, is extremely difficult, and is currently based primarily on expensive, non-representative microbial sampling methods.

Typically, food processing equipment, such as freezers and ovens, are periodically scheduled for cleaning and then sanitizing with chemicals. Quantification of the efficacy of chemical sanitizing is normally not possible in an industrial setting. The variability of coverage of chemicals, contact times, starting numbers of bacteria, and other factors affecting the action of cleaning chemicals against bacteria are too great to make quantification of efficacy possible on the large scale required in food processing plants. Thus, to quantify a sanitation level of the food processing equipment that has undergone chemical sanitizing, expensive, non-representative microbial sampling must be conducted, as discussed above.

An alternative approach to chemical sanitizing is sanitizing through thermal destruction of bacteria. Steam in particular, if applied correctly to large pieces of equipment, can be effective in killing bacteria in a uniform and predictable manner. For example, U.S. Pat. No. 6,264,889B1 describes an apparatus and method for microbial intervention and pasteurization of food processing equipment using steam. The method applies steam to food items or food processing equipment so as to raise the surface temperature of food items or food processing equipment. Once the surface temperature rises to a certain temperature, for example 74° C., the temperature is maintained at that level for a certain period of time, for example, 60 seconds. After that, chilled water at about 2–5° C. is sprayed onto the food items or food processing equipment. It is claimed that alternating heating and cooling of the food items or food processing equipment can provide a five log reduction (100,000 times) in the amount of microbial pathogens on the surfaces of food items or food processing equipment. This method, however, is not capable of continuously monitoring the sanitation level in food processing equipment throughout its use, including those times when the equipment is in normal use and is not being sanitized. In other words, while the method is directed to achieving a certain sanitation level immediately after sanitizing, it is silent as to how to monitor and control sanitation level of food processing equipment during its normal use, especially after some time has lapsed since its last sanitizing.

In reality, however, bacteria on the surfaces of food processing equipment can grow (or die) over time. Thus, while procedures that help determine (and/or control) the number of bacteria on some area of food processing equipment at a single point in time can be helpful, these procedures do not address the fact that bacterial levels are changing continuously. A more thorough approach would require continuous monitoring of the sanitation level of any equipment at all times, not just during or right after sanitizing. Therefore, a need exists for a method and system for continuously monitoring and controlling the sanitation level in food processing equipment.

SUMMARY OF THE INVENTION

The present invention discloses a new method of modeling sanitation levels in food processing equipment, including, for example, food freezers, ovens, conveyors, and portioners. The method uses the growth and death models of bacteria of interest to calculate (estimate) the bacterial level in the food processing equipment over time.

Specifically, the invention provides a method of creating a sanitation level model with respect to a predefined microorganism in food processing equipment. The method of creating a sanitation level model includes generally three steps. First, a temperature history during a use cycle of the food processing equipment is created. The temperature history includes a collection of a plurality of temperatures that the food processing equipment undergoes during the use cycle. The use cycle includes a normal use stage, a sanitizing stage, and perhaps an idle stage. Second, a growth model of the microorganism is continuously applied to each applicable temperature in the temperature history. Third, a death model of the microorganism is continuously applied to each applicable temperature in the temperature history. The created sanitation level model indicates the microorganism growth/death rate (trend) in the food processing equipment during the use cycle.

In accordance with one aspect of the invention, the sanitizing stage involves thermal sanitizing, for example, by using steam.

In accordance with another aspect of the invention, if the created sanitation level model indicates that the food processing equipment has been operated at a less than desirable level of sanitation, such indication can be used as a basis for controlling (or adjusting) the temperature parameters of the food processing equipment (e.g., what maximum temperature should be used during sanitizing or how long that maximum temperature should be maintained). In a particular example, the temperature parameters may be adjusted so that the estimated destruction of the microorganism during the sanitizing stage exceeds the estimated potential growth of the microorganism during the normal stage in order to achieve an overall negative growth environment for the microorganism.

In accordance with a further aspect of the invention, to increase the accuracy of the sanitation level model, actual sampling of the microorganism may be obtained from the food processing equipment during the use cycle, and the results of the actual sampling may be introduced to the sanitation level model.

A plurality of sanitation level models may be created with respect to a plurality of microorganisms, respectively, to calculate the levels of the plurality of microorganisms in the food processing equipment.

In accordance with a still further aspect of the present invention, a system is provided for modeling a sanitation level with respect to a predefined microorganism in food processing equipment. The system includes a temperature monitor thermally coupled to the food processing equipment. The system also includes a processor coupled to the temperature monitor. The processor is adapted to execute computer-readable instructions for performing the following three steps: (a) defining a temperature history of the food processing equipment based on the temperature obtained from the temperature monitor; (b) continuously applying a growth model of the microorganism to the temperature history; and (c) continuously applying a death model of the microorganism to the temperature history. As before, the created sanitation level model can be used for monitoring the microorganism growth/death rate in the food processing equipment.

The system may also be adapted to continuously record the created sanitation level model concerning the food processing equipment. The record may be used to provide historical data on the sanitation level of the food processing equipment, which can then be used as a basis for validating and warranting the sanitation level of the food processing equipment.

In summary, the present invention provides a method and system for continuous application of microbial growth and death models for managing the hygiene and sanitation of food processing equipment. Especially when the food processing equipment is sanitized using a thermal method, both growth and death models may be used to continuously and reliably calculate the bacterial level on the surfaces of the food processing equipment. This method could be used to calculate how to optimally operate and sanitize food processing equipment to reduce the amount of any bacteria to an acceptable level. Furthermore, the method can be used to provide information necessary for validating or warranting the sanitation level of the food processing using the equipment.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

The present invention provides a method of creating a sanitation level model with respect to a predefined microorganism in food processing equipment, such as a freezer, oven, portioner, slabber, trimmer, conveyor, slicer, hopper, grader, scale, and packaging equipment. Specifically, the method may generally include three steps. First, a temperature history is created to represent the change in temperature during a use cycle of the food processing equipment. The temperature history includes a collection of a plurality of temperatures that the food processing equipment undergoes during the use cycle. The use cycle includes at least two stages: a normal use stage wherein the food processing equipment is used for its intended purposes; and a sanitizing stage wherein the food processing equipment is sanitized. Normally, many food processing devices also undergo a cleaning stage just prior to the sanitizing stage. Further, many devices undergo an idle stage in which the devices are taken out of use, for example, over a weekend for a number of hours or even days, after the cleaning stage and/or the sanitizing stage prior to being put back into the normal use stage. Second, a growth model of the microorganism is continuously applied to each applicable temperature in the temperature history. Third, a death model of the microorganism is continuously applied to each applicable temperature in the temperature history. The growth and death models of various microorganisms at various temperatures are available from the United States Department of Agriculture (USDA) and other sources. The continuous application of both growth and death models of the microorganism of interest, such as bacteria, allows the resulting sanitation level model to show the microorganism level in the food processing equipment over time. In other words, the sanitation level model can be used to indicate the microorganism growth/death rate in the food processing equipment during the use cycle of the equipment.

Figure 1:
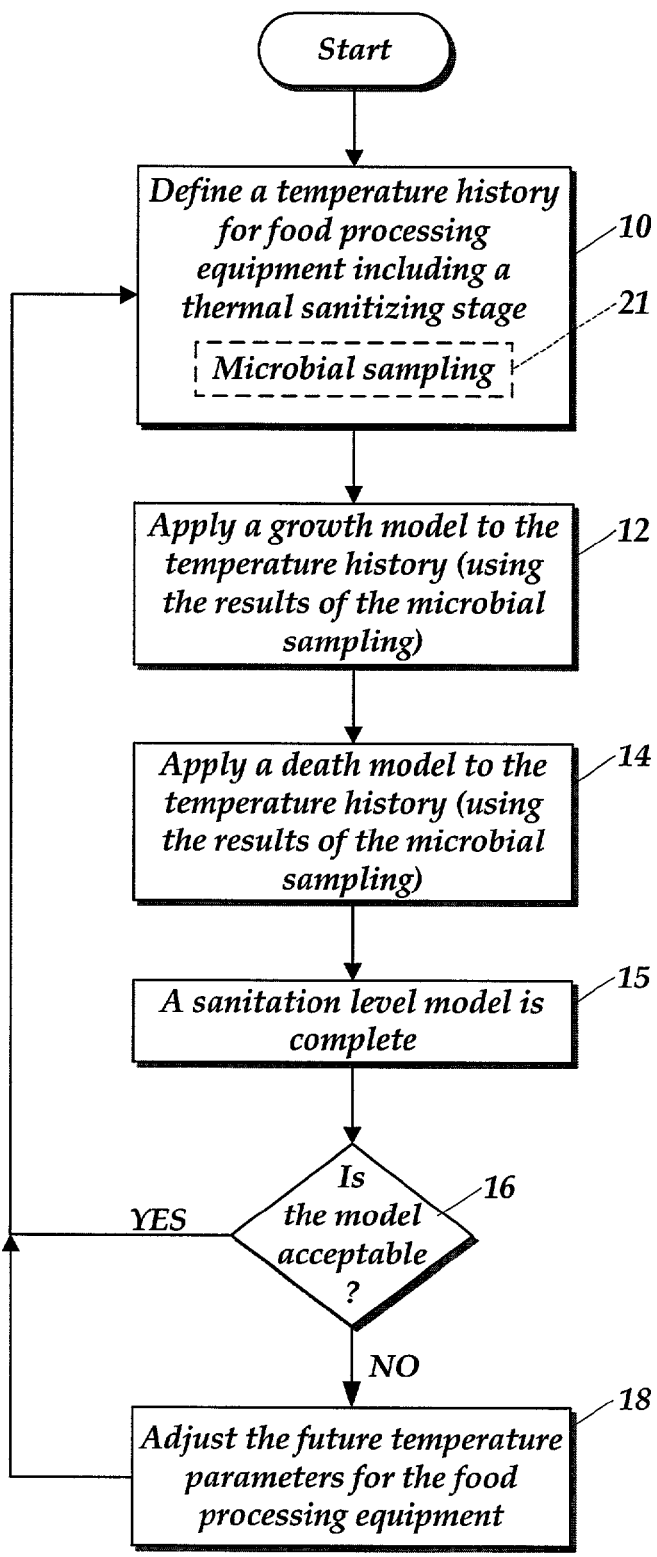
FIG. 1 is a flow chart illustrating a method of creating a sanitation level model of a predefined microorganism in food processing equipment, according to the present invention.
Figure 2:
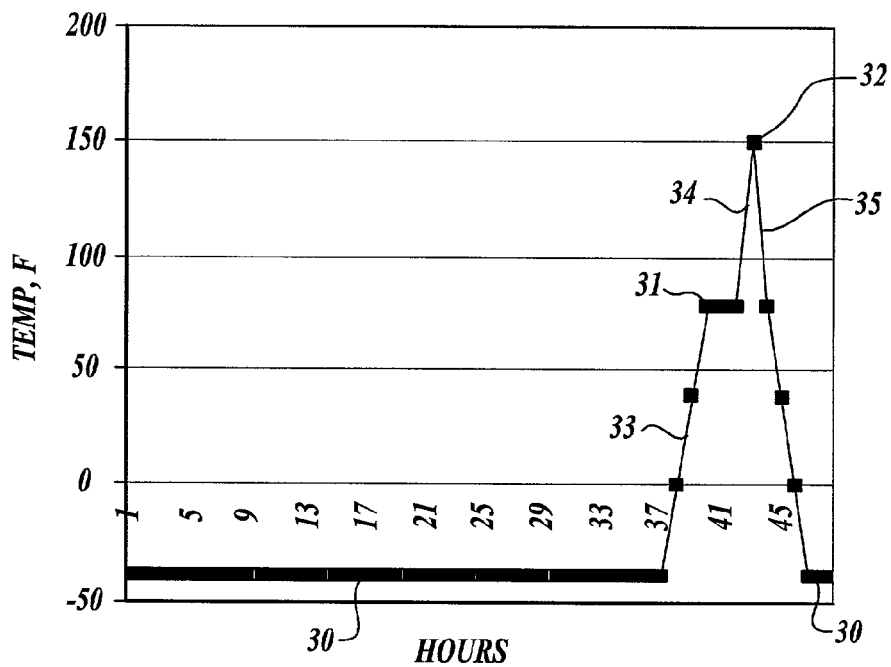
FIG. 2 is a sample temperature history of a freezer during its use cycle.

FIG. 1 is a flow chart illustrating one embodiment of a method of creating a sanitation level model in accordance with the present invention. At block 10, a temperature history for food processing equipment is defined by continuously obtaining the temperature of the food processing equipment using any suitable temperature monitor means. In this embodiment, the food processing equipment is scheduled to undergo thermal sanitizing. Typically, certain temperature parameters, such as the maximum temperature to be reached during sanitizing or how long that maximum temperature should be maintained, are predefined prior to the operation of the equipment. FIG. 2 illustrates a sample temperature history for a freezer, suitable for use in a method of the present invention. Referring to FIG. 2, during its normal use stage 30, the freezer was kept at its normal use temperature of approximately −40° F. (from 0–37$^{th}$ hour). The freezer was then temporarily taken out of use and thawed for cleaning and sanitizing purposes. In the temperature history, during a cleaning stage 31, the freezer was held at approximately 95° F. for about three hours (39–42$^{nd}$ hour). Cleaning typically involves removing any contamination deposited during the operation of the food processing equipment, such as particles, fats, oils, proteins, etc., from the surfaces of the food processing equipment until the surfaces are visually clean. The freezer then went through thermal sanitizing stage 32 (by steam, for example) at approximately 149° F. for five minutes. Thermal sanitizing may be carried out using any other suitable thermal means, such as by using dry heat provided by a radiator coil into which steam or thermal fluid is introduced. Once sanitizing was complete, the temperature of the freezer was quickly reduced to approximately −40° F. again and the freezer was put back into its normal use 30. As shown in FIG. 2, the temperature history also includes several transition stages 33, 34 and 35, wherein the temperature was changing.

Figure 3:
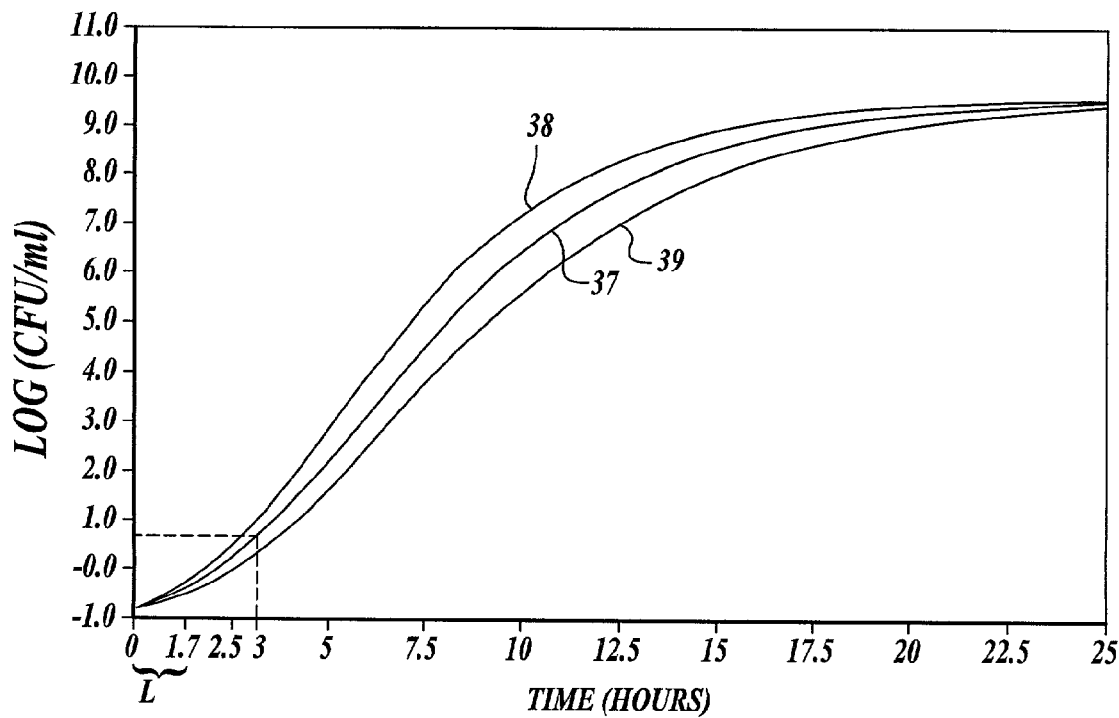
FIG. 3 is a graph showing growth model curves of Listeria monocytogenes.
Figure 4:
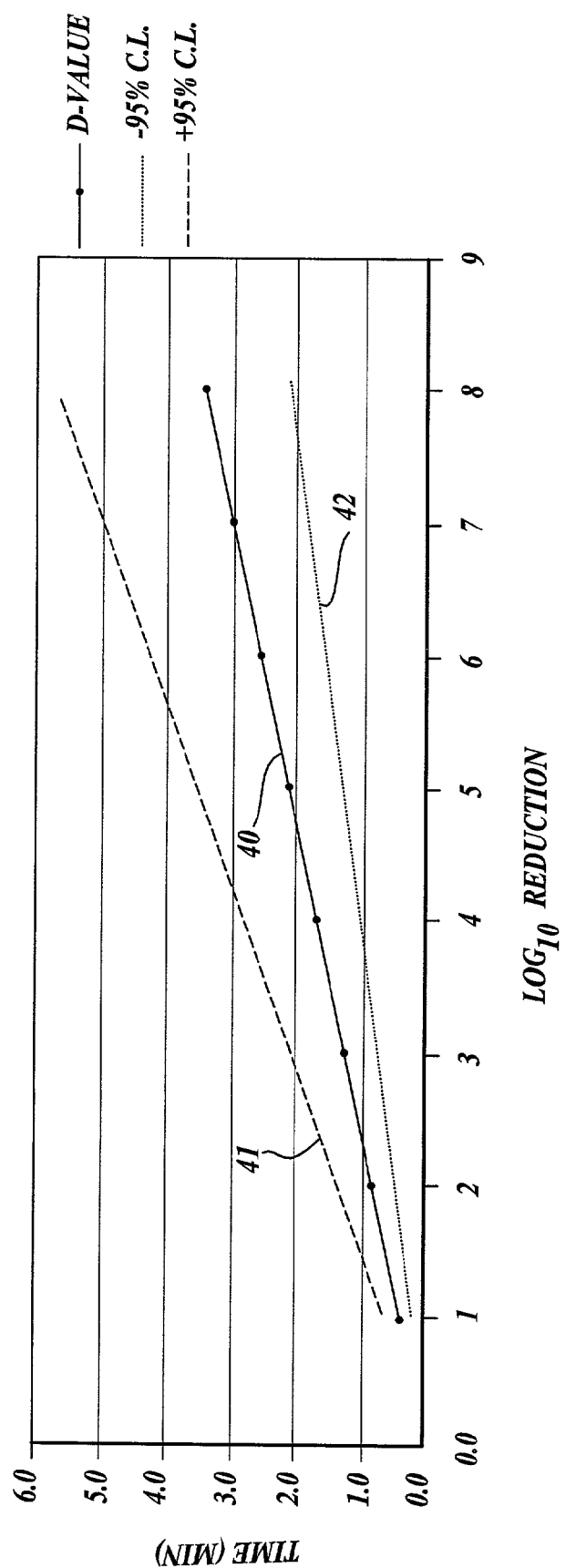
FIG. 4 is a graph showing death model curves of Listeria monocytogenes.

Referring back to FIG. 1, once the temperature history for the food processing equipment is defined, or perhaps as the temperature history is being defined, in block 12, a growth model of the microorganism of interest is applied to the temperature history. Likewise, in block 14, a death model of the microorganism of interest is applied to the temperature history. FIG. 3 is a graph showing growth model curves of Listeria monocytogenes and FIG. 4 is a graph showing death model curves of Listeria monocytogenes. Both graphs were developed and are available from the USDA. FIG. 3 shows growth curves at 95° F., at pH 6.5, water activity at maximum (equaling 0.997), and without sodium nitrate. The lag phase L wherein very little growth occurs is given at 1.7 hours, and generation time is 0.3 hours. Generation time is the time for the amount of the bacteria (Listeria monocytogenes in this case) to double. Therefore, in this case, at 95° F., the bacteria are doubling about every 18 minutes. As well understood by those skilled in the art, the growth model in FIG. 3 consists of three subcurves: a middle confidence level curve 37; a +95% (higher) confidence level curve 38; and a −95% (lower) confidence level curve 39. These curves represent the growth model of the bacteria at different confidence levels.

Referring back to FIG. 2, the freezer was held at approximately 95° F. for three hours during the cleaning stage 31. To apply the growth curve of FIG. 3 (or, more specifically, the middle confidence level curve 37) to the cleaning stage 31, the only unknown is the starting amount of Listeria. However, if we assume even the worst case for this model, for example assuming three logs per square centimeters of starting bacteria at the beginning of the cleaning stage 31, at 95° F., after three hours (at the end of the cleaning), we would have only an increase in one log, resulting in four logs of bacteria per square centimeters (see FIG. 3, showing less than one-log increase in three hours).

FIG. 4 is a death model curve of Listeria monocytogenes, again consisting of three subcurves: a mid-confidence level curve 40; a +95% (higher) confidence level curve 41; and −95% (lower) confidence level curve 42. FIG. 4 shows death curves at temperature 149° F., with pH 6.5 and no phosphate and no salt. As well known in the art, the "D-value" referred to in FIG. 4 represents the time (in minutes) at a particular temperature (149° F. in this case) that is required to kill 90% of the target microorganism, i.e. the time that is necessary to achieve a one-log reduction. Since the D-value is fixed, the death model "curves" are actually linear, as illustrated. Again referring additionally to the temperature history of FIG. 2, the freezer's temperature was raised to about 149° F. for five minutes during the sanitizing stage 32. Looking at FIG. 4, thermal sanitizing at this level would give a predicted seven- to eight-log reduction in bacteria. Therefore, four-log bacteria that may have been present at the end of the cleaning stage 31, assuming the worst case, are calculated to be effectively eliminated during the thermal sanitizing stage 32.

After growth/death models are applied to the temperature history, a sanitation level model is complete (block 15 in FIG. 1).

While a sanitation level model has been described above as being formed by continuously applying a growth model and a death model of a microorganism to each applicable temperature in a temperature history, it should be understood that the application of a growth and/or death model may be performed in a different order, alternating order, or even concurrently. For example, both growth and death models may be first combined to create an overall "population change" model, and this model may then be applied to the temperature history (thus, both growth and death models are being applied to the temperature history "concurrently" in a sense.) Therefore, steps 12 and 14 of FIG. 1 do not represent a sequential order for performing this invention but rather, indicate the necessary processing that must be completed to generate a sanitation level model of the present invention. Accordingly, as used in the present invention, the steps of "continuously applying a growth model of a microorganism to each applicable temperature in a temperature history" and "continuously applying a death model of a microorganism to each applicable temperature in a temperature history" encompass all cases wherein growth and death models are applied to a temperature history, regardless of a manner or order in which the models are applied (e.g., regardless of a particular algorithm used to apply the models).

Still referring to FIG. 2, during the normal use stage 30, at this temperature level of −40° F., the growth of the bacteria (Listeria monocytogenes) is close to zero. Therefore, repeating the normal use stage 30, cleaning stage 31, and the sanitizing stage 32 continuously will result in a negative growth environment for the bacteria. Specifically, during each sanitizing stage, more bacteria are expected to be killed than the amount of bacteria that may have grown in between sanitizing stages, resulting in a very low bacteria level in the freezer throughout its use cycle. Given a large enough difference between predicted growth and predicted death, the actual levels of starting bacteria become unimportant as the use cycle is repeated. As this example demonstrates, the growth and death models could be applied to the temperature history of food processing equipment over any length of time (hours, days, months).

As will be apparent to those skilled in the art, growth and death model curves for the same microorganism vary depending on the environment, such as the temperature, the pH level, the water activity (the measure of "free" or "available" water; the higher the measure of free water, the higher the growth rate of any microorganism), and levels of various other chemical substances. The growth and death models also vary depending on the type of the material on (or in) which the bacteria of interest are present (for example, stainless steel in the case of the surfaces of typical food processing equipment). When creating a sanitation level model, one way of deciding which growth or death model to use would be to take a "conservative" approach, i.e., to assume the environment that is most desirable for the growth of the microorganism, or least desirable for the death of the microorganism. Then, one may select either a growth curve or a death curve to meet that criterion for each applicable temperature in the temperature history.

In the previous example, we have ignored the transition stages 33, 34, and 35 in FIG. 2 wherein the temperature of the freezer was changing. In another embodiment of a method of the present invention, growth and death models of the bacteria may be continuously applied to these stages (33, 34, and 35) also, to more accurately model the actual growth and death of the bacteria. For example, in stage 33, assuming that the temperature was rising from 39° F. to 40° F. in one minute, we can calculate the bacteria growth during this minute using a growth curve corresponding to the "conservative" temperature of 40° F., since at this temperature range more bacteria growth is expected at a higher temperature (40° F.). We will do the same for the next minute wherein the temperature was rising from 40° F. to 41° F., using a growth curve of 41° F., and so on. Likewise, in stage 34, if the temperature was rising from 130° F. to 131° F. in one minute, we can calculate the log reduction of the bacteria during this minute using a death curve model corresponding to the "conservative" temperature of 130° F., since at this temperature range less bacteria death is expected at a lower temperature (130° F.).

As will be apparent to those skilled in the art, there are numerous other ways to continuously apply growth and death models to the temperature history as shown in FIG. 2. For example, if the temperature was changing from 130° F. to 140° F. in 10 minutes, one may apply a death model of the average temperature (135° F.) during that time. Therefore, the term "continuous application" or "continuously applying" as used in the present application is intended to encompass various applications of growth and death models during the use cycle of food processing equipment. For example, referring to FIG. 2, "continuous application" of growth and death models may mean selecting a few temperatures at which the equipment was held for a period of time, namely, the temperatures of the normal use stage 30, the cleaning stage 31, and the sanitizing stage 32, and applying respective growth and death models to those temperatures only. In another example, still referring to FIG. 2, "continuous application" of growth and death models may mean, in addition to applying the models to the three temperature-stationary stages 30, 31, and 32, applying growth and death models also to the transition stages 33, 34, and 35 using various temperature intervals, averaging methods, etc.

Figure 5:
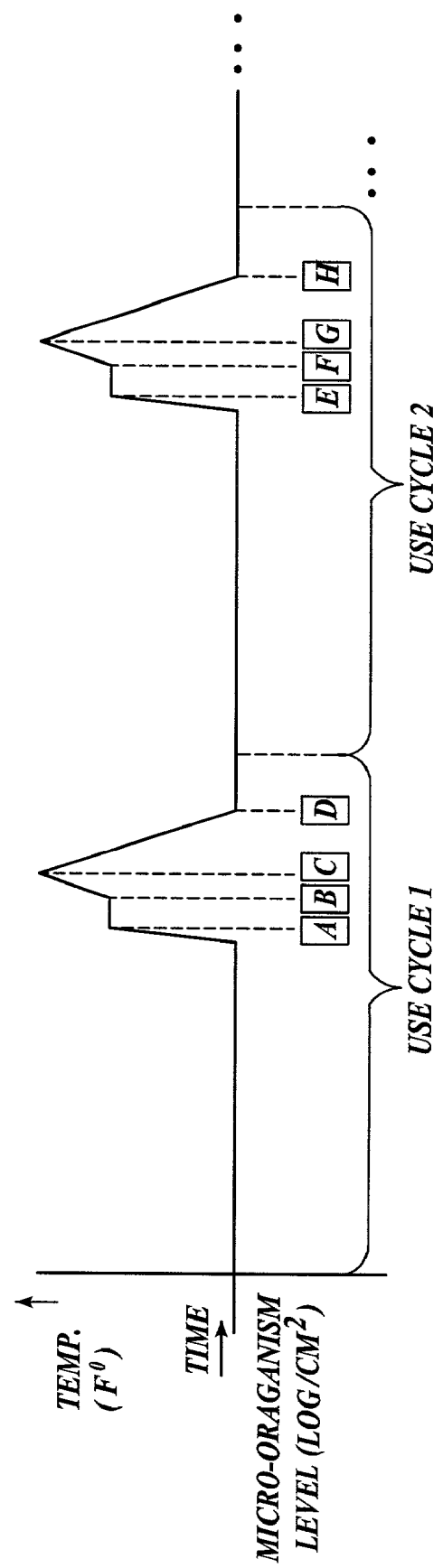
FIG. 5 is a schematic representation of a sanitation level model created in accordance with the present invention.

FIG. 5 is a schematic representation of a sanitation level model, created in accordance with the present invention. The model indicates the predicted level of the microorganism A-H (in log/cm$^2$, for example) at various points in time during the repeated use cycles of the food processing equipment (two cycles are shown). By comparing the microorganism levels between any two time points, one may ascertain the overall microorganism growth/death rate during the use cycle of the food processing equipment. Ascertaining the microorganism growth/death rate helps ensure a negative growth environment for the microorganism, in which more microorganisms are expected to be killed than the amount of microorganisms that may grow, resulting in a very low microorganism level throughout the use cycle. The predicted levels of the microorganism are calculated based on the continuous application of growth and death models to the temperature history, as described above.

Referring additionally to FIG. 1, optionally in block 21, actual sampling of the microorganism may be taken from the surfaces of the food processing equipment during the use cycle (i.e., as the temperature history is being defied) to determine the sanitation level of the equipment (for example, by swabbing the surfaces). If this step is taken, in blocks 12 and 14, the result of such microbial sampling can be used to provide a starting or ending number of bacteria at any given point in time during the use cycle. (For example, any of actual microorganism levels A-H in FIG. 5 may be provided based on the results of microbial sampling.) Incorporating the results of microbial sampling when applying growth/death models to the temperature history allows the resulting sanitation level model to further accurately reflect the sanitation level of the food processing equipment.

In general, the more continuously the growth and death models are applied, the more accurate the calculated level of the bacteria becomes. The accurate model in turn helps avoid having to use excessive energy during the sanitizing stage. Specifically, when the actual bacteria level cannot be accurately calculated (estimated), a conservative approach would require applying excessive heat during thermal sanitizing, only to achieve bacteria overkill. This is undesirable not only because it wastes energy, but also because the excessive heat may damage the food processing equipment itself. For example, raising the temperature of a freezer to 170° F. would be sufficient to almost instantly kill any pathogens that may be present, but such high temperature may also damage the freezer itself. The more preferable approach would be to set the maximum sanitizing temperature at a lower level (e.g., 149° F.) but then to hold the freezer at the lower temperature for a longer period. A method of the present invention allows for creating a sanitation level model, and further allows for controlling the future temperature parameters of the food processing equipment based on the created sanitation level model, order to devise an optimal method of operating and sanitizing food processing equipment, as will become apparent from the description below.

Specifically, referring back to FIG. 1, once the growth and death models are applied to the temperature history to create a sanitation level model (block 15), in block 16, it is determined whether the created sanitation level model is acceptable. This may be done manually by an operator verifying that, according to the created sanitation level model such as is shown in FIG. 5, the destruction of the microorganism during the sanitizing stage exceeds the potential growth of the microorganism during the normal use stage and other non-sanitizing stages. Further, the operator may ensure that the maximum thermal sanitizing temperature does not exceed a predefined level so as to avoid damaging the food processing equipment. Alternatively, the verification of any type may be made automatically using a processor used to create the sanitation level model, as more fully discussed below. If the sanitation level model is acceptable, the method loops back to block 10 and continues defining a temperature history and creating a sanitation level model based on the temperature history. On the other hand, if the sanitation level model is not acceptable, proceeding to block 18, the future temperature parameters (e.g., a sanitizing temperature or how long that temperature should be kept) in the operation of the food processing equipment can be adjusted, so as to achieve a desired sanitation level. Thereafter, going back to block 10, the temperature history continues to be defined as the food processing equipment is operated based on the adjusted temperature parameters, and in blocks 12 and 14, growth and death models are applied to the temperature history. Thus, the created sanitation level model is used not only to continuously monitor the sanitation level of the food processing equipment but also to continuously optimize the operation (including sanitizing) of the food processing equipment to maintain or achieve a desired sanitation level.

Figure 6:
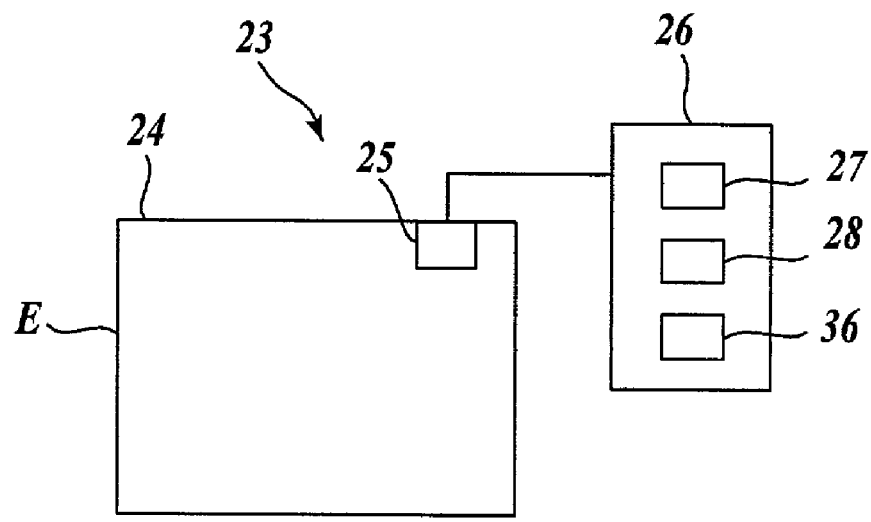
FIG. 6 is a schematic illustration of a system for creating a sanitation level model of a predefined microorganism in food processing equipment, wherein the equipment is suited for thermal sanitizing.

FIG. 6 schematically illustrates a system 23 for creating a sanitation level model of a microorganism in food processing equipment, suitable for use in performing a method of the present invention, wherein the food processing equipment is thermally sanitized. The system 23 is coupled to a food processing equipment 24, such as a freezer or an oven, including an enclosure E that can contain heat to effect any thermal sanitizing method. (Means for effecting thermal sanitizing are not shown.) The system 23 includes a temperature monitor 25 coupled to the food processing equipment 24 to measure its temperature. The temperature monitor 25 may be any device that is adapted to measure the temperature of the food processing equipment 24, such as a thermocouple or a remote infrared sensor. The system 23 also includes a control unit 26, including a processor 27, a user interface 28, and a memory 36. The processor 27 is adapted to execute computer-readable instructions for performing various steps involved in the method of the present invention. The user interface 28 includes conventional input device (keyboard, touch screen, etc.) and output device (screen, etc.). The memory 36 comprises any suitable data recording medium, some of which may be removable, for storing the instruction for the processor 27 and also any data related to the sanitation level of a microorganism.

According to a method of the present invention, the control unit 26 of the system 23 defines the temperature history (block 10 in FIG. 1) based on the temperature obtained from the temperature monitor 25, and applies growth and death models to the temperature history (blocks 12 and 14 in FIG. 1). Some user intervention via the user interface 28 may be allowed at this time, for example selection of particular growth/death models to be applied or a manner in which the selected growth/death models are continuously applied to the temperature history. Alternatively, blocks 10, 12, and 14 of FIG. 1 may be performed fully automatically based on predefined instructions using growth/death models prestored in the memory 36. The control unit 26 thus creates a sanitation level model, and perhaps displays the resulting sanitation level model (as shown in FIG. 5) on a screen of the user interface 28. For example, calculated bacteria levels at various points during the use cycle of the food processing equipment may be displayed, so that an operator can ascertain the bacterial growth/death rate in the food processing equipment to decide whether it is acceptable and, if not, control (adjust) the future temperature parameters in the operation of the food processing equipment (from block 16 to block 18 in FIG. 1). Alternatively, the validation of the resulting sanitation level model may be performed automatically by the control unit 26, for example by the processor 27 checking to see if a bacterial growth rate at any time period during the use cycle exceeds a predefined threshold level.

The sanitation level model (such as shown in FIG. 5) may be recorded in the memory 36 of the control unit 26 to collect historical data. For example, the historical data may be later presented in a report form for the purpose of review, or for the purpose of validating or warranting the sanitation level of the food processing equipment to meet any regulatory standards.

According to a method of the present invention as applied to food processing equipment that is kept cold (for example, freezer, refrigerator, etc.), when such equipment undergoes a systematic process of heating by thermal sanitizing (for example, using steam) and cooling during its normal use, the basic assumption of microorganism levels on the surfaces of the equipment becomes fairly reliable and reasonably realistic. In other words, a sanitation level model created for this type of equipment can be used to ascertain (or ensure) that the repeated cycle of heat with high death rate, and cold with very low growth rate, produces a negative growth environment for bacteria on the surfaces of the equipment. Maintaining a negative growth environment greatly reduces the likelihood of bacteria ever growing to very high numbers in any area of the equipment, and thus greatly reduces the possibility of food becoming contaminated with the bacteria. This aspect of the present invention is particularly effective in addressing the issue of controlling bacteria growth in "harborages" of food processing equipment. A harborage is an area in food processing equipment that never gets cleaned, usually due to equipment design. Thus, bacteria in a harborage would normally grow to very high levels over a long period of time (days, weeks, or even months) and continuously contaminate the food being processed, if an environment is such as to allow for bacterial growth. According to the present invention, however, a sanitation level model can be used to create (or ensure) a negative growth environment for the bacteria based on temperature manipulation (e.g., repeated cycle of heat with high death rate and cold with very low growth rate) in order to retard bacterial growth in even those harborage areas. This is possible partly because a thermal sanitizing method (for example, the steaming technique) can achieve very uniform heating throughout the food processing equipment (including some harborage areas), and hence reliable death of bacteria.

For the same reasons, a method of the present invention may be applied equally well to food processing equipment whose temperature is kept high, such as an oven. When an oven is in normal use, the temperature is kept sufficiently high to quickly kill any bacteria that may be present. An oven, however, must also periodically go through cleaning and sanitizing. The temperature of the oven is lowered during cleaning, and bacteria may grow at this lowered temperature. A thermal sanitizing following cleaning, however, may be calculated to achieve much higher log reduction in bacteria than the potential bacteria growth during the cleaning stage, thereby again achieving a negative growth environment for the bacteria. Therefore, generally, food processing equipment including an enclosure, which allows for continuous operation of the equipment at a sufficiently high or cold temperature and also allows for application of a thermal sanitizing method, is well suited for use with a method of the present application described above.

Certain food processing equipment, such as a freezer or an oven, includes a "cold" hold or "hot" hold feature. For example, a freezer with a "cold" hold feature is designed so that the freezer can be kept at a cold temperature even when it is not in use. Likewise, an oven with a "hot" hold feature is designed so that it can be kept at a high temperature even when it is not in use. According to a method of the invention, one may hold the temperature of such food processing equipment intentionally low or high, using the "cold" hold or "hot" hold feature, to inhibit any growth of bacteria or kill any bacteria, respectively. Such artificial manipulation of the temperature can be reflected in the temperature history (see FIG. 2) and hence into the sanitation level model. For example, the "cold" or "hot" hold feature may be advantageously activated during an idle stage of a use cycle, during which the food processing equipment is taken out of use after cleaning or sanitizing. Use of the "cold" or "hot" hold feature during the idle stage retards growth of bacteria or kills bacteria, and thus the equipment needs not be cleaned or sanitized again prior to being put back into a normal use stage. Manipulating the temperature of the food processing equipment in this matter to control bacterial growth/death thereon allows for optimal overall operation of the food processing equipment throughout the use cycle, not just during or immediately after the sanitizing stage.

Some food processing equipment does not include an enclosure, and therefore is not suited for thermal sanitizing method. For example, a conveyor, portioner, slabber, trimmer, slicer, hopper, grader, scale, and packaging equipment usually do not include any enclosure, and therefore are typically sanitized using a chemical sanitizing method. One approach for applying a method of the present invention described above to these types of equipment would be to enclose such equipment inside a container that can trap heat so that a thermal sanitizing method can be applied. Another approach would be to apply a modified version of a method of the present invention.

Figure 7:
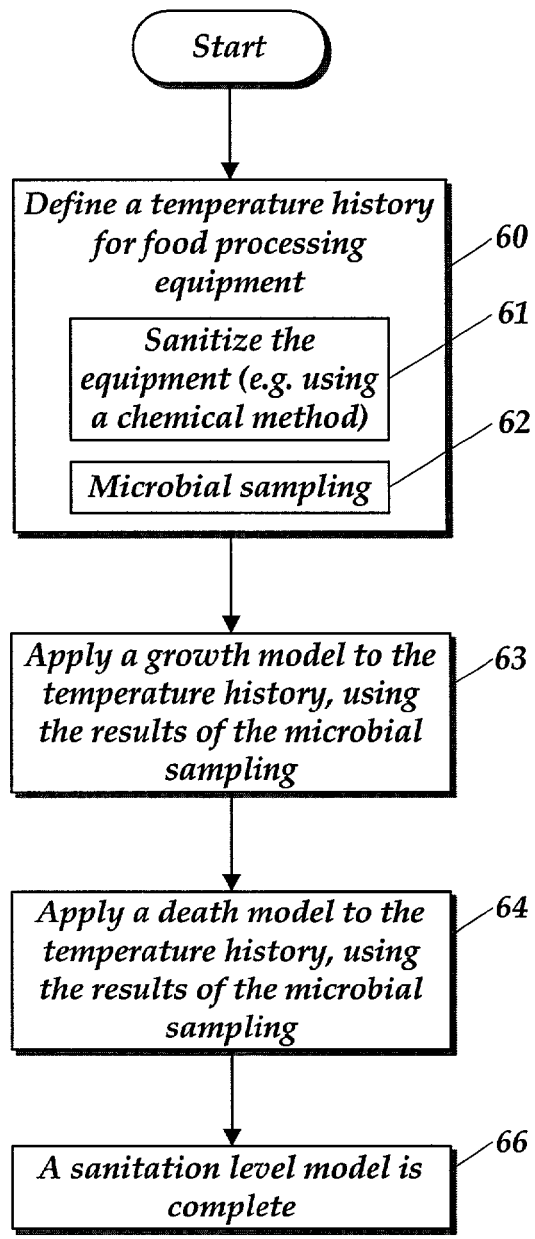
FIG. 7 is a flow chart illustrating a method of creating a sanitation level model in accordance with a second embodiment of the present invention.

Specifically, FIG. 7 is a flow chart illustrating another embodiment of a method of the present invention, suitable for use with food processing equipment that is designed to undergo non-thermal sanitizing method (for example, a chemical sanitizing method). In block 60, a temperature history for the food processing equipment is defined. Since the equipment does not include any enclosure, the temperature history would tend to be fairly flat, probably coinciding with the ambient temperature history. Still, a method of the present invention of modeling the sanitation level, based on a temperature history, will work as long as the temperature of equipment surfaces is relatively uniform and stable. As the temperature history is being defined (block 60), in block 61, the food processing equipment is sanitized using a non-thermal sanitizing method, such as a chemical method. As discussed in the background section, quantification of the effect of chemical sanitizing is normally not possible in an industrial setting due to various uncertain factors, such as the variability of coverage of chemicals, contact times, and starting numbers of a bacteria. Therefore, microbial sampling is carried out in block 62. Specifically, actual sampling of bacteria is taken from the surfaces of the food processing equipment to determine the actual bacteria level of the equipment. Thereafter in block 63, a growth model is continuously applied to the temperature history (including the period during which the non-thermal sanitizing (block 61) was carried out), using the results of the microbial sampling. In block 64, a death model is continuously applied to the temperature history, again using the results of the microbial sampling. In block 66, a sanitation level model is complete. In one embodiment, an "assumed" death model for chemical sanitizing is further applied in creating a sanitation level model. An assumed death model due to chemical sanitizing is generated by analyzing historic (cumulative) data of microbial sampling before and after chemical sanitizing. A generated assumed death model can then be applied to the chemical sanitizing stage of the use cycle.

The created sanitation level model is used to continuously monitor the sanitation level of the food processing equipment, and also to possibly adjust the future temperature parameters in the operation of the equipment, similarly to the method of the first embodiment described above.

Figure 8:
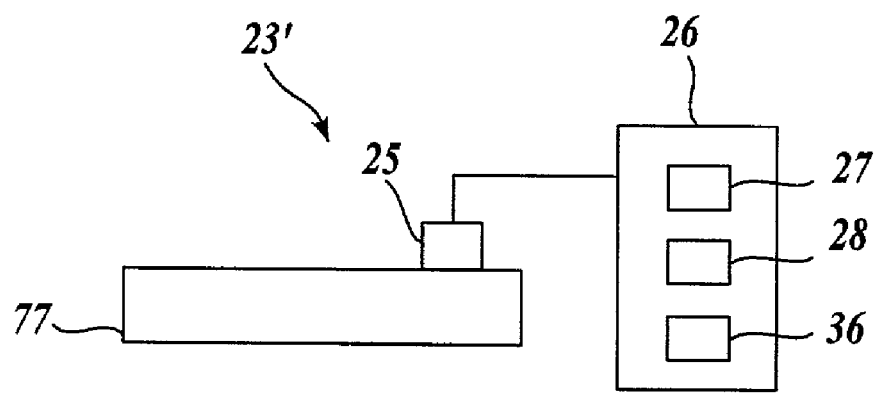
FIG. 8 is a schematic illustration of a system for implementing the method of FIG. 7, wherein the food processing equipment is not suited for thermal sanitizing.

FIG. 8 illustrates a system suitable for implementing a method described in FIG. 7. The system is similar to the system 23 described in FIG. 5, and the same parts are identified using the same reference numbers. Specifically, in FIG. 87 the system 23' is coupled to food processing equipment 77, which is not suited for thermal sanitizing. The system 23' includes a temperature monitor 25 and a control unit 26, which in turn includes a processor 27, a user interface 28, and a memory 36. The detailed description of the operation of the system 23' is omitted, as it is similar to the operation of the system 23 described in reference to FIG. 5.

According to a method of the present invention, growth and death models of bacteria are applied to calculate the sanitation level of food processing equipment continuously. This continuous modeling will allow for control over the environment and temperature of the equipment to ensure that the destruction of bacteria during sanitizing always greatly exceeds the potential growth of bacteria during food processing (normal use), cleaning, or any other periods of downtime when bacteria can grow. To minimize the potential growth of bacteria and further increase the reliability of the sanitation level model, cleaning time during which bacteria may grow should be minimized. For example, in the temperature history of FIG. 2, the freezer was kept at 95° F. during the cleaning stage 31 for only approximately three hours. To reduce the amount of time necessary to clean food processing equipment, such equipment should preferably include a feature or option that allows the equipment to be cleaned relatively quickly. Various food processing equipment, for example freezers, chillers, and proofers, including such a fast cleaning option (termed "fast Clean-In-Place (CIP)" capability), are available under the trademark of GYRoCOMPACT® from Frigoscandia, Inc. of Redmond, Wash.

While a method of the present invention has been described using an example of Listeria monocytogenes, it should be understood by those skilled in the art that a method can be applied to create a sanitation level model with respect to any of a variety of microorganisms. A common list of pathogenic microorganisms of interest in the food processing industry includes *Salmonella* spp., *Clostridium botulinum, Staphylococcus aureus, Campylobacter jejuni, Yersinia enterocolitica* and *Yersinia pseudotuberculosis, Listeria monocytogenes, Vibrio cholerae* O1, *Vibrio cholerae* non-O1, *Vibrio parahaemolyticus* and other vibrios, *Vibrio vulnificus, Clostridium perfringens, Bacillus cereus, Aeromonas hydrophila* and other spp., *Plesiomonas shigelloides, Shigella* spp., miscellaneous enterics, and *Streptococcus*. A method may also be applied to create a sanitation level model with respect to a variety of non-pathogenic microorganisms, such as spoilage organisms and indicator organisms.

According to a method of the present invention, a plurality of sanitation level models may be created with respect to a plurality of predefined microorganisms, respectively. In this case, once a temperature history is defined, growth and death models of respective microorganisms are separately applied to create separate sanitation level models, and these models are used to ascertain or monitor the growth or death rates of the plurality of microorganisms, respectively, in the food processing equipment.

As briefly described before, a method of the present invention is well suited for validation and warranty purposes. Specifically, as discussed in the background section, producers of cooked meat and poultry products are increasingly being required to produce documented, science-based validations and warranties of the sanitation level of their processes. The sanitation level model generated using a method of the present invention and stored in the memory 36 of the control unit 26 can be readily used to provide the bases for validating and warranting the sanitation level of the processes.

The embodiments of the invention in which an exclusive property is claimed are defined as follows:

1. A method of creating a sanitation level model with respect to a predefined microorganism in food processing equipment, comprising:
   a. creating a temperature history during a use cycle of the food processing equipment, the temperature history comprising a collection of a plurality of temperatures that the food processing equipment undergoes during the use cycle, the use cycle comprising a normal use stage and a sanitizing stage;
   b. continuously applying a growth model of the microorganism to each applicable temperature in the temperature history; and
   c. continuously applying a death model of the microorganism to each applicable temperature in the temperature history;
   wherein the created sanitation level model is used to ascertain the microorganism growth/death rate in the food processing equipment during the use cycle.

2. The method of claim 1, wherein the food processing equipment is selected from the group consisting of a freezer and an oven.

3. The method of claim 1, wherein the food processing equipment is selected from the group consisting of a conveyor, a portioner, a slabber, a trimmer, a slicer, a hopper, a grader, a scale, and packaging equipment.

4. The method of claim 1, wherein the microorganism comprises a pathogen selected from the group consisting of *Salmonella* spp., *Clostridium botulinum*, *Staphylococcus aureus*, *Campylobacter jejuni*, *Yersinia enterocolitica* and *Yersinia pseudotuberculosis*, *Listeria monocytogenes*, *Vibrio cholerae* O1, *Vibrio cholerae* non-O1, *Vibrio parahaemolyticus* and other vibrios, *Vibrio vulnificus*, *Clostridium perfringens*, *Bacillus cereus*, *Aeromonas hydrophila* and other spp., *Plesiomonas shigelloides*, *Shigella* spp., miscellaneous enterics, and *Streptococcus*.

5. The method of claim 1, wherein the microorganism comprises a spoilage organism or an indicator organism.

6. The method of claim 1, wherein the sanitizing stage comprises thermal sanitizing.

7. The method of claim 6, wherein the thermal sanitizing comprises application of steam to the food processing equipment.

8. The method of claim 1, wherein the use cycle further comprises an idle stage, and the food processing equipment comprises a temperature hold feature that is activated during the idle stage.

9. The method of claim 1, wherein the sanitizing stage comprises chemical sanitizing.

10. The method of claim 9, further comprising the steps of:
    obtaining actual sampling of the microorganism from the food processing equipment during the use cycle; and
    introducing the results of the actual sampling to the sanitation level model.

11. The method of claim 9, further comprising the steps of:
    creating an assumed death model due to chemical sanitizing based on analysis of historic data of microbial sampling before and after chemical sanitizing; and
    applying the assumed death model to the sanitizing stage of the use cycle.

12. The method of claim 1, further comprising the step of controlling temperature parameters in the operation of the food processing equipment based on the created sanitation level model to ensure that the destruction of the microorganism determined based on the death model exceeds the potential growth of the microorganism determined based on the growth model.

13. The method of claim 1, further comprising the steps of:
    obtaining actual sampling of the microorganism from the food processing equipment during the use cycle; and
    introducing the results of the actual sampling to the sanitation level model.

14. The method of claim 1, wherein a plurality of sanitation level models are created with respect to a plurality of predefined microorganisms, respectively, and steps b. and c. are performed for each of the plurality of predefined microorganisms, wherein the created plurality of sanitation level models are used to ascertain the growth/death rates of the plurality of predefined microorganisms, respectively, in the food processing equipment.

15. A system for creating a sanitation level model of a predefined microorganism in food processing equipment, the system comprising:
    a temperature monitor thermally coupled to the food processing equipment; and
    a processor coupled to the temperature monitor, the processor loaded with computer-readable instructions for performing the steps of:
    a. creating a temperature history during a use cycle of the food processing equipment by obtaining the temperature of the food processing equipment from the temperature monitor, the temperature history comprising a collection of a plurality of temperatures that the food processing equipment undergoes during the use cycle, the use cycle comprising a normal use stage and a sanitizing stage;
    b. continuously applying a growth model of the microorganism to each applicable temperature in the temperature history; and
    c. continuously applying a death model of the microorganism to each applicable temperature in the temperature history.

16. The system of claim 15, wherein the food processing equipment is selected from the group consisting of a freezer, oven, conveyor, portioner, slabber, trimmer, slicer, hopper, grader, scale, and packaging equipment.

17. The system of claim 15, wherein the microorganism comprises a pathogen selected from the group consisting of *Salmonella* spp., *Clostridium botulinum*, *Staphylococcus aureus*, *Campylobacter jejuni*, *Yersinia enterocolitica* and *Yersinia pseudotuberculosis*, *Listeria monocytogenes*, *Vibrio cholerae* O1, *Vibrio cholerae* non-O1, *Vibrio parahaemolyticus* and other vibrios, *Vibrio vulnificus*, *Clostridium perfringens*, *Bacillus cereus*, *Aeromonas hydrophila* and other spp., *Plesiomonas shigelloides*, *Shigella* spp., miscellaneous enterics, *Streptococcus*.

18. The system of claim 15, wherein the microorganism comprises a spoilage organism or an indicator organism.

19. The system of claim 15, wherein the processor is adapted to execute computer-readable instructions for performing the further step of continuously recording the created sanitation level model of the food processing equipment.

* * * * *